US00PP15078P3

(12) United States Plant Patent
Spink

(10) Patent No.: US PP15,078 P2
(45) Date of Patent: Aug. 17, 2004

(54) DIEFFENBACHIA PLANT NAMED 'NICOLETTE'

(50) Latin Name: *Dieffenbachia hybrida*
Varietal Denomination: Nicolette

(75) Inventor: Gary Spink, Wellington Point (AU)

(73) Assignee: Futura Promotions Pty. Ltd. (AU)

( * ) Notice: Subject to any disclaimer, the term of this patent is extended or adjusted under 35 U.S.C. 154(b) by 155 days.

(21) Appl. No.: 10/245,835

(22) Filed: Sep. 17, 2002

(65) Prior Publication Data

US 2004/0055066 P1 Mar. 18, 2004

(51) Int. Cl.[7] ..... A01H 5/00

(52) U.S. Cl. ..... Plt./378

(58) Field of Search ..... Plt./378

*Primary Examiner*—Bruce R. Campell
*Assistant Examiner*—Susan B. McCormick
(74) *Attorney, Agent, or Firm*—Paul S. Rooy, P.A.

(57) ABSTRACT

'Nicolette', a Dieffenbachia cultivar. 'Nicolette' is characterized by small size elliptic leaves, moderate to good suckering ability, and short petiole and petiole wing clasping the stem to about the leaf base. Leaves are yellow green with a green border having a distinctive fish-bone like pattern of yellow-green extending into the border.

2 Drawing Sheets

Latin name of the genus and species of the plant claimed: The plant genus is Dieffenbachia. The plant species is hybrida.

FIELD OF THE INVENTION

The present invention comprises a new and distinct cultivar of Dieffenbachia which is named 'Nicolette'. Its genus is Dieffenbachia. The plant species is hybrida. Its market class is that of ornamental potted plants. 'Nicolette' is a perennial plant, and is intended for use in landscaping, and as a decorative potted plant.

DESCRIPTION OF PRIOR ART

'Nicolette' is the product of a planned breeding program carried out in 1993 and 1994 at Wellington Point, Queensland, Australia. Its parents were wild Dieffenbachia. 'Nicolette' was the product of a planned breeding program carried out by the Inventor Gary R. Spink in 1993 and 1994. Nicolette's pollen parent was Dieffenbachia 'Tropic Marianne' (U.S. Plant Pat. No. 8,832), and its seed parent was Dieffenbachia 'Triumph' (not subject of a U.S. Plant Patent).

As compared to parental variety 'Tropic Marianne', the growth habit of 'Nicolette' is smaller and more compact (height 60 cm, width 60 cm) than 'Tropic Marianne'. 'Tropic Marianne' is taller and not so compact (height 90 cm, width 90 cm). The leaf shape of 'Nicolette' is elliptic, while the leaf shape of 'Tropic Marianne' is oblong. The leaf apex shape of 'Nicolette' is acute-sharply pointed, while the leaf apex shape of 'Tropic Marianne' is rounded with small point. The leaf size of 'Nicolette' is small (23.3 cm long and 12.24 cm wide, yielding a length to width ratio of 1.9), while the leaf size of 'Tropic Marianne' is larger (35.5 cm long by 20.67 cm wide, yielding a length to with ratio of 1.72). Note a smaller length to width ratio indicates a wider leaf. The 'Nicolette' distance from apex of wing to leaf base is 1.6 cm, while the 'Tropic Marianne' distance from apex of wing to leaf base 8.5 cm.

As compared to parental variety 'Triumph', the leaves of 'Triumph' are smaller than those of 'Nicolette'. 'Triumph' has a colored petiole (Orange White about RHS 159B–C) whereas Nicolette has a green petiole. 'Triumph' has a dark green leaf wing which is speckled whereas that of 'Nicolette' has no speckling. 'Nicolette' leaves are yellow-green with a border of green. 'Nicolette's' leaf border has the yellow-green of the leaf extending into it, forming a distinctive fish-bone like pattern. 'Triumph' has no fish bone pattern. The 'Triumph' petiole wings tightly clasp the stem whereas the petiole wings of 'Nicole' don't.

As compared to 'Nicole' (described in co-pending application Ser. No. 10/245,834), the 'Nicole' leaves (31.0 cm long by 13.2 cm wide, yielding a length to width ratio of 2.38), are larger than the 'Nicolette' leaves (23.2 cm long by 12.24 cm wide, yielding a length to width ratio of 1.9). 'Nicolette' plants are smaller and more compact (60 cm high, 60 cm wide), than 'Nicole' plants (70 cm high, 90 cm wide). The 'Nicolette' apex of wing to leaf base distance is 1.6 cm, while the 'Nicole' apex of wing to leaf base distance is 2.7 cm.

Uniformity

Dieffenbachia 'Nicolette' was first asexually reproduced in September 1994 by vegetative cutting. The plant is a perennial. The plant is stable as evidenced by propagation over more than five generations, using vegetative cuttings, over a period of more than five years. Propagation was carried out at Wellington Point, Queensland, Australia.

No off-types have been observed throughout the trial period. The variety is considered to be uniform and stable in all characteristics.

SUMMARY OF THE INVENTION

The major characteristics of 'Nicolette' include small size elliptic leaves, moderate to good suckering ability and short petiole and petiole wing clasping the stem to about the leaf base. Leaves are yellow-green with a green border having a distinctive fish-bone like pattern of yellow-green extending into the border.

The following traits which have been repeatedly observed are determined to be basic characteristics of 'Nicolette', which in combination distinguish 'Nicolette' from other Dieffenbachia of the same general type.

1. Plant growth habit is small and compact: height 60 cm, width 60 cm.
2. Leaf shape is elliptic.
3. Leaf size is 23.2 cm long and 12.24 cm wide. The length to width ratio is 1.9.
4. Leaves are yellow-green with a border of green. The border has the yellow-green of the leaf extending into it forming a distinctive fish-bone like pattern.
5. The distance from apex of wing to leaf base is 1.6 cm.

BRIEF DESCRIPTION OF THE DRAWINGS

The invention, together with the other objects, features, aspects and advantages thereof will be more clearly understood from the following in conjunction with the accompanying drawings.

Two sheets of drawings are provided. Sheet one contains FIG. 1. Sheet two contains FIG. 2.

BOTANICAL DESCRIPTION OF THE PLANT

Figure 1:
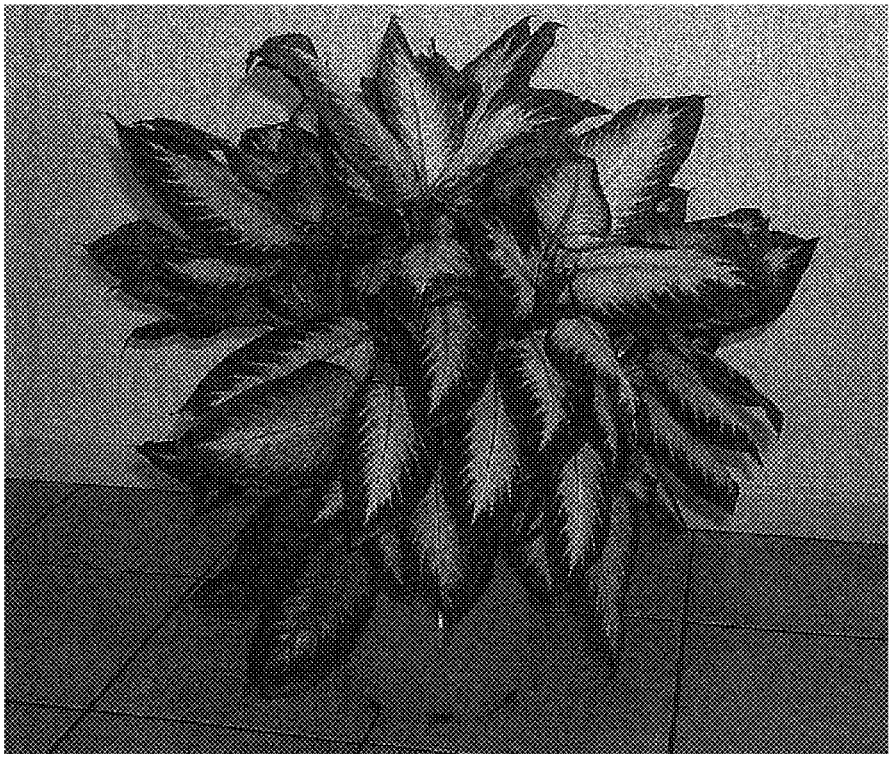
FIG. 1 is a color photograph of a front view of 'Nicolette'.
Figure 2:
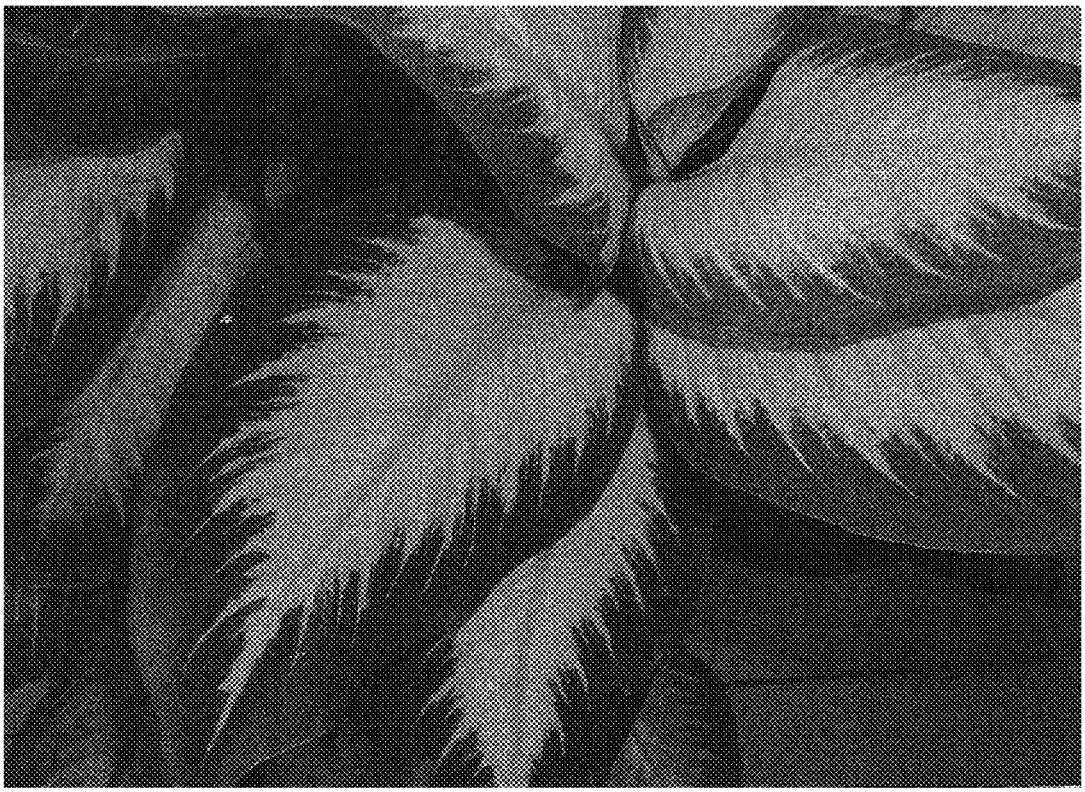
FIG. 2 is a color photograph of a close-up view of 'Nicolette' leaves.

FIGS. 1 and 2 depict a Dieffenbachia 'Nicolette' in a 250 mm pot grown from a single vegetative cutting (12 weeks old) after 40 weeks under greenhouse growing conditions. This 'Nicolette' was about 60 cm high measured from soil surface to the tip, and about 60 cm wide.

The following Botanical Description describes Dieffenbachia 'Nicolette' plants grown at Wellington Point, Queensland, Australia grown under greenhouse growing conditions. The plant has not been observed under all possible environmental conditions. The phenotype may vary somewhat with variations in environment such as temperature, light intensity and/or fertilizer rate, without, however, any variance in genotype.

'Nicolette' will withstand minimum night temperatures of 10 degrees centigrade for short periods of time. Maximum daytime temperatures of 40 degrees centigrade are tolerated, if sufficient shading is given.

Stem:

*Growth pattern.*—The mature stem is approximately 2.0 cm to 2.4 cm in diameter about 5 cm above the soil level. Inter-node distance is approximately 2.0–3.0 cm at soil level in mature stems.

*Color.*—The stem is light green RHS 139D and speckled with dark green RHS 139A–B.

Petiole: The following information is based on the second expanded leaf from the apex.

*Growth pattern.*—The petiole has fleshy edges (wings) extending from midrib. The wings are approximately 10 mm to 15 mm wide one-half the distance from the petiole base to the wing apex. The apex of the wing is emarginated, about 5 mm wide at the tip.

*Dimensions.*—Petiole length is 11.3 cm on average, and ranges from 10 cm to 15 cm. Wing length is 9.7 cm on average, and ranges from 9.5 cm to 11 cm. The distance between leaf base to tip of apex ranges from 1 cm to 1.6 cm.

*Color.*—The petiole wings (abaxial) are yellow green RHS 146B, which gradually fades towards mid rib into much lighter yellow green RHS 145D. The abaxial surface of the mid rib is yellow green RHS 145A at base and apex, and between fades to a white RHS 155A.

Leaves: Dieffenbachia 'Nicolette' has small sized elliptic leaves. The leaves are yellow green with a green border having a distinctive fish-bone like pattern of yellow green extending into the border.

*Growth pattern.*—The leaf is elliptic with an obtuse base with entire margin. The leaf is asymmetric with the side of the leaf unrolling first having less surface area than the side unrolling last. The leaf is oriented parallel to the stem axis at the time of full unrolling, changing to substantially horizontal to stem. The mid rib is straight over the length of the leaves.

*Dimensions.*—The leaf is approximately 23.2 cm long and 12.24 cm wide, having a length to width ratio of 1.9.

*Midrib.*—Prominent and attractive.

*Primary veins.*—The primary veins are sunken into the upper surface and protrude out of the underside.

*Color and pattern.*—The adaxial surface of new leaves has a midrib color of white RHS 155A in the middle tending to yellow green RHS 145A at the apex and base. With maturity more green creeps into the white sections. The edges are dark green RHS 139A, and the mid section is yellow green RHS 145A, blending into white RHS 155A at midribs and main veins. The abaxial surface is lighter than the adaxial surface. The edges are RHS 137B, and the middle is RHS 145A at the apex, fading to RHS 145C at the base. The midrib is yellow green RHS 146C–D.

*Auxiliary breaks.*—Moderate to good suckering ability.

Inflorescence: The inflorescence is made up of spadix and a spathe. The spadix consists of an upright central axis covered with several minute flowers without petals. Female flowers consists of a stigma, style and ovary, while the male flowers (anther and filament) produce the pollen.

Roots: Thick white roots with fine laterals. Root initiation of cuttings under optimal growing conditions begins after two weeks. Liners are ready to pot after 12 weeks.

Fruit and seed: No fruit or seed have been observed under normal greenhouse conditions.

All color codes refer to "The Royal Horticultural Society London, 1995 Ed.". Colors and leaf size may vary somewhat depending on horticultural practices such as light levels and fertilizer rates, among other things, without however, any variance in genotype.

I claim:

1. A new and distinct cultivar of Dieffenbachia plant named 'Nicolette', as herein described and illustrated.

* * * * *